(12) United States Patent
Freiman et al.

(10) Patent No.: US 11,602,321 B2
(45) Date of Patent: Mar. 14, 2023

(54) SPECTRAL INFLAMMATION MAP FROM SPECTRAL IMAGING DATA

(71) Applicant: KONINKLIJKE PHILIPS N.V., Eindhoven (NL)

(72) Inventors: Mordechay Pinchas Freiman, Zichron-Yaakov (IL); Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 117 days.

(21) Appl. No.: 17/041,172

(22) PCT Filed: Mar. 22, 2019

(86) PCT No.: PCT/EP2019/057184
§ 371 (c)(1),
(2) Date: Sep. 24, 2020

(87) PCT Pub. No.: WO2019/185457
PCT Pub. Date: Oct. 3, 2019

(65) Prior Publication Data
US 2021/0007698 A1    Jan. 14, 2021

Related U.S. Application Data

(60) Provisional application No. 62/647,865, filed on Mar. 26, 2018.

(51) Int. Cl.
*G06T 7/00* (2017.01)
*G06T 15/08* (2011.01)
*A61B 6/00* (2006.01)

(52) U.S. Cl.
CPC ............ *A61B 6/5217* (2013.01); *A61B 6/463* (2013.01); *A61B 6/482* (2013.01); *G06T 7/0012* (2013.01);
(Continued)

(58) Field of Classification Search
CPC ....... A61B 6/482; A61B 6/5217; A61B 6/463; G06T 7/0012; G06T 15/08; G06T 2207/10081; G06T 2207/30004
See application file for complete search history.

(56) References Cited

U.S. PATENT DOCUMENTS 9,538,971 B2    1/2017    Alessio
2004/0136491 A1    7/2004    Iatrou
(Continued)

FOREIGN PATENT DOCUMENTS

WO    WO2016171570 A1    10/2016

OTHER PUBLICATIONS

Clark DP, Holbrook M, Badea CT. Multi-energy CT decomposition using convolutional neural networks. In Medical Imaging 2018: Physics of Medical Imaging Mar. 9, 2018 (vol. 10573, p. 1057310). International Society for Optics and Photonics. (Year: 2018).*

(Continued)

*Primary Examiner* — Diane M Wills
(74) *Attorney, Agent, or Firm* — Larry Liberchuk (57) ABSTRACT

A system (300) includes a memory (324) configured to store an inflammation map generator module (328). The system further includes a processor (322) configured to: receive at least one of spectral projection data or spectral volumetric image data, decompose the at least one of spectral projection data or spectral volumetric image data using a two-basis decomposition to generate a set of vectors for each basis represented in the at least one of spectral projection data or spectral volumetric image data, compute a concentration of each basis within a voxel from the set of vectors for each basis, and determine a concentration of at least one of fat or inflammation within the voxel from the concentration of (Continued)

each basis. The system further includes a display configured to display the determined concentration of the at least one of fat or inflammation.

20 Claims, 5 Drawing Sheets (52) U.S. Cl.
CPC .... *G06T 15/08* (2013.01); *G06T 2207/10081* (2013.01); *G06T 2207/30004* (2013.01)

(56) References Cited

U.S. PATENT DOCUMENTS

| | | | |
|---|---|---|---|
| 2007/0217570 | A1 | 9/2007 | Grasruck |
| 2014/0133729 | A1* | 5/2014 | Goshen ................. A61B 6/482 382/131 |
| 2015/0272527 | A1* | 10/2015 | Narayanan ............ A61B 6/481 382/131 |
| 2018/0114314 | A1* | 4/2018 | Butler ................... A61B 6/482 |

OTHER PUBLICATIONS

PCT International Search Report, International application No. PCT/EP2019/057184, dated Jun. 7, 2019.
Alessio A. M. et al., "Quantitative Material Characterization from Multi-Energy Photon Counting CT", Medical Physics, AIP, Melville, NY, US, vol. 40, No. 3, Mar. 1, 2013 (Mar. 1, 2013).
Amor S. et al., "Inflammation in Neurodegenerative Diseases", Immunology, vol. 129, No. 2. pp. 154-169, 2010.
Amor S. et al., "Inflammation in Neurodegenerative Diseases—an Update", Immunology, vol. 142, No. 2. pp. 151-166, 2014.
Golia E. et al., "Inflammation and Cardiovascular Disease: from Pathogenesis to Therapeutic Target", Current Atherosclerosis Reports, vol. 16, No. 9. 2014.
Coussens L. M. et al., "Inflammation and Cancer", Nature, vol. 420, No. 6917, pp. 860-867, 2002.
Grivennikov S.I. et al., "Immunity, Inflammation, and Cancer", Cell, vol. 140, No. 6, pp. 883-899, 2010.
Hammod D.A. et al., "Molecular Imaging of Inflammation: Current Status", The Journal of Nuclear Medicine, vol. 57, No. 8, pp. 1161-1166, Aug. 2016.
McCpllough C.H. et al., "Dual- and Multi-Energy CT: Principles, Technical Approaches, and Clinical Applications" Radiology, vol. 276, No. 3, pp. 637-653, 2015.
Motiei M. et al., "Differentiating between Cancer and Inflammation: A Metabolic-Based Method for Functional Computed Tomography Imaging", American Chemical Society (ACS) Nano, vol. 10, No. 3, pp. 3469-3477, 2016.
Nakanishi K. et al., "Augmented Inflammation in Pericoronary Adipose Tissue is Associated with Future Acute Coronary Syndrome in Patients with Coronary Artery Disease," European Heart Journal, vol. 34, No. suppl_1, p. 154, Aug. 2013.
Antonpoulos A. S. et al., "Detecting Human Coronary Inflammation by Imaging Perivascular Fat", Science Translational Medecine, vol. 9, No. 398, Jul. 2017.
Patino M. et al., "Material Separation Using Dual-Energy CT: Current and Emerging Application", Radiographics, vol. 36, No. 4, Jul. 11, 2015.
Boussel L. et al., "Photon counting spectral CT component analysis or coronary artery atherosclerotic plaque samples", British Institute of Radiology, 2014.
Baturin P. et al., "Spectral CT Imaging of Vulnerable Plaque with Two Independent Biomarkers", Physics in Medicine and Biology, vol. 57, 2012.

* cited by examiner

SPECTRAL INFLAMMATION MAP FROM SPECTRAL IMAGING DATA

FIELD OF THE INVENTION

The following generally relates to imaging and more particularly to generating a spectral inflammation image from spectral imaging data, and is described with particular application to computed tomography imaging.

BACKGROUND OF THE INVENTION

Inflammation is considered to be associated with many types of diseases including neurodegenerative, cardiovascular, and cancer. Non-invasive inflammation detection methods may therefore support early disease detection when the damage caused by the disease may still be reversible, improved patient stratification, and response to treatment assessment. Imaging inflamed tissue via nuclear medicine techniques, such as imaging radiolabeled white blood cells and 18F-fluorodeoxyglucose (18F-FDG) with positron emission tomography (PET), can provide information about the inflammation reaction. However, this technique is limited due to the large amount of radiation dose involved, limited availability, high costs, limited spatial and temporal resolution, and limited ability to distinguish between highly metabolized healthy organs, such as the heart, and nearby inflammation.

Figure 1:
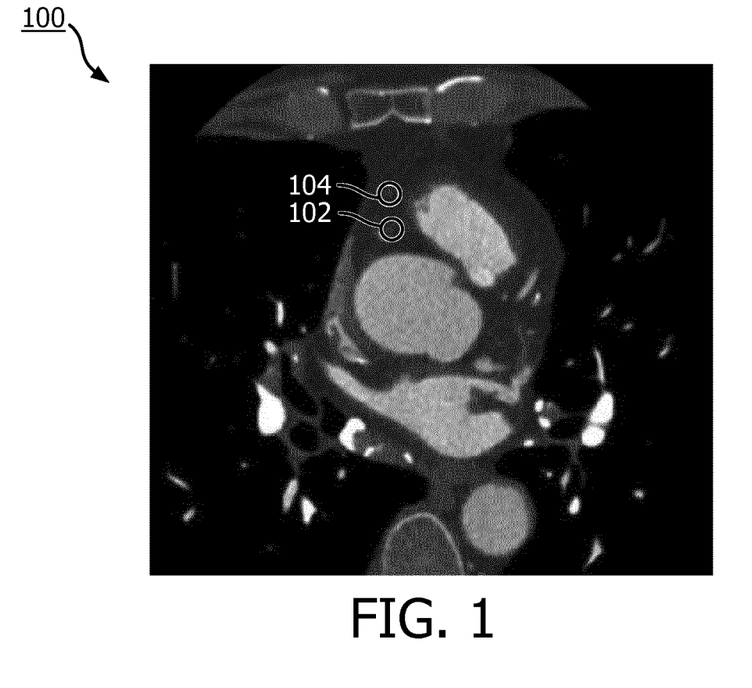
FIG. 1 illustrates an example CT image of a heart with one region of interest including mostly fat and another region of interest including mostly inflammation.
Figure 2:
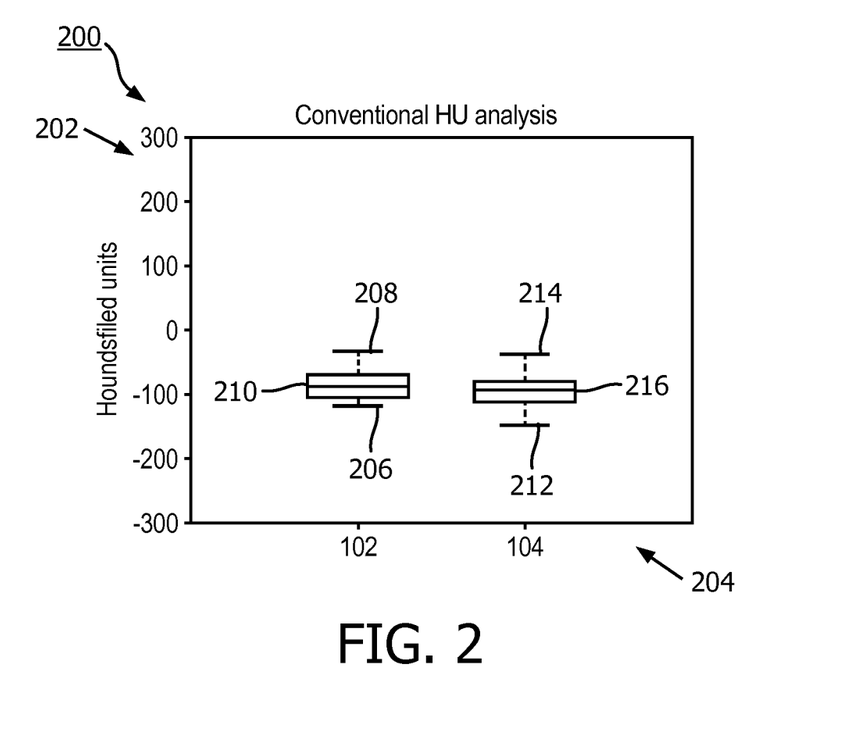
FIG. 2 illustrates an example box plots for the regions of interest in the image shown in FIG. 1.

Imaging inflamed tissue with computed tomography (CT) provides information about structural tissue changes. These changes include edema, the accumulation of fluid in the extracellular space, contrast enhancement, endothelial disruption, and organ damage. However, CT has a limited ability to characterize inflammation due to low contrast between healthy tissue and/or fat, inflammation and imaging artifacts including beam-hardening. For example, FIG. 1 depicts a CT image 100 of a heart with a first region of interest (ROI) 102 and a second ROI 104. The first region of interest 102 is known to have high inflammation with little to no fat concentration, and the second region of interest 104 is known to have little or no inflammation and a high fat concentration. FIG. 2 presents box plots 200 for the ROI's 102 and 104.

In FIG. 2, a first axis 202 represents Hounsfield unit (HU) values and a second axis 204 represents the ROI's. FIG. 2 shows, for the first ROI 102, a minimum value 206, a maximum value 208, and a median value 210, and, for the second ROI 104, a minimum value 212, a maximum value 214, and a median value 216. The box plots 200 show that while there may be a difference in median HU values 210 and 216 between the two ROI's 102 and 104, the difference is not statistically significant. As such, inflammation is commonly assessed through delayed enhancement in contrast-enhanced CT scans, which depict mainly vascular permeability associated with increased inflammation. Unfortunately, these changes are subjectively determined and difficult to quantify, e.g., due to various imaging artifacts including beam-hardening, low contrast between healthy tissue and inflammation, etc.

SUMMARY OF THE INVENTION

Aspects described herein address the above-referenced problems and others.

Described herein is an approach to assess inflammation by generating a spectral map which depicts and quantifies inflammation in spectral volumetric image data (e.g., CT).

In one aspect, a system includes a memory configured to store an inflammation map generator module. The system further includes a processor configured to: receive at least one of spectral projection data or spectral volumetric image data, decompose the at least one of spectral projection data or spectral volumetric image data using a two-basis decomposition to generate a set of vectors for each basis represented in the at least one of spectral projection data or spectral volumetric image data, compute a concentration of each basis within a voxel from the set of vectors for each basis, and determine a concentration of at least one of fat or inflammation within the voxel from the concentration of each basis. The system also includes a display configured to display the determined concentration of the at least one of fat or inflammation.

In another aspect, a method includes receiving at least one of spectral projection data or spectral volumetric image data, and decomposing the at least one of spectral projection data or spectral volumetric image data using a two-basis decomposition to generate a set of vectors for each basis represented in the at least one of spectral projection data or spectral volumetric image data. The method further includes computing a concentration of each basis within a voxel from the set of vectors for each basis, determining a concentration of at least one of fat or inflammation within the voxel from the concentration of each basis, and displaying display the determined concentration of the at least one of fat or inflammation.

In another aspect, a computer readable storage medium encoded with computer readable instructions, which, when executed by a processor of a computing system, causes the processor to receive at least one of spectral projection data or spectral volumetric image data, and decompose the at least one of spectral projection data or spectral volumetric image data using a two-basis decomposition to generate a set of vectors for each basis represented in the at least one of spectral projection data or spectral volumetric image data. The computer readable instructions, which when executed by the processor further causes the processor to compute a concentration of each basis within a voxel from the set of vectors for each basis, determine a concentration of at least one of fat or inflammation within the voxel from the concentration of each basis, and display the determined concentration of the at least one of fat or inflammation.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 3:
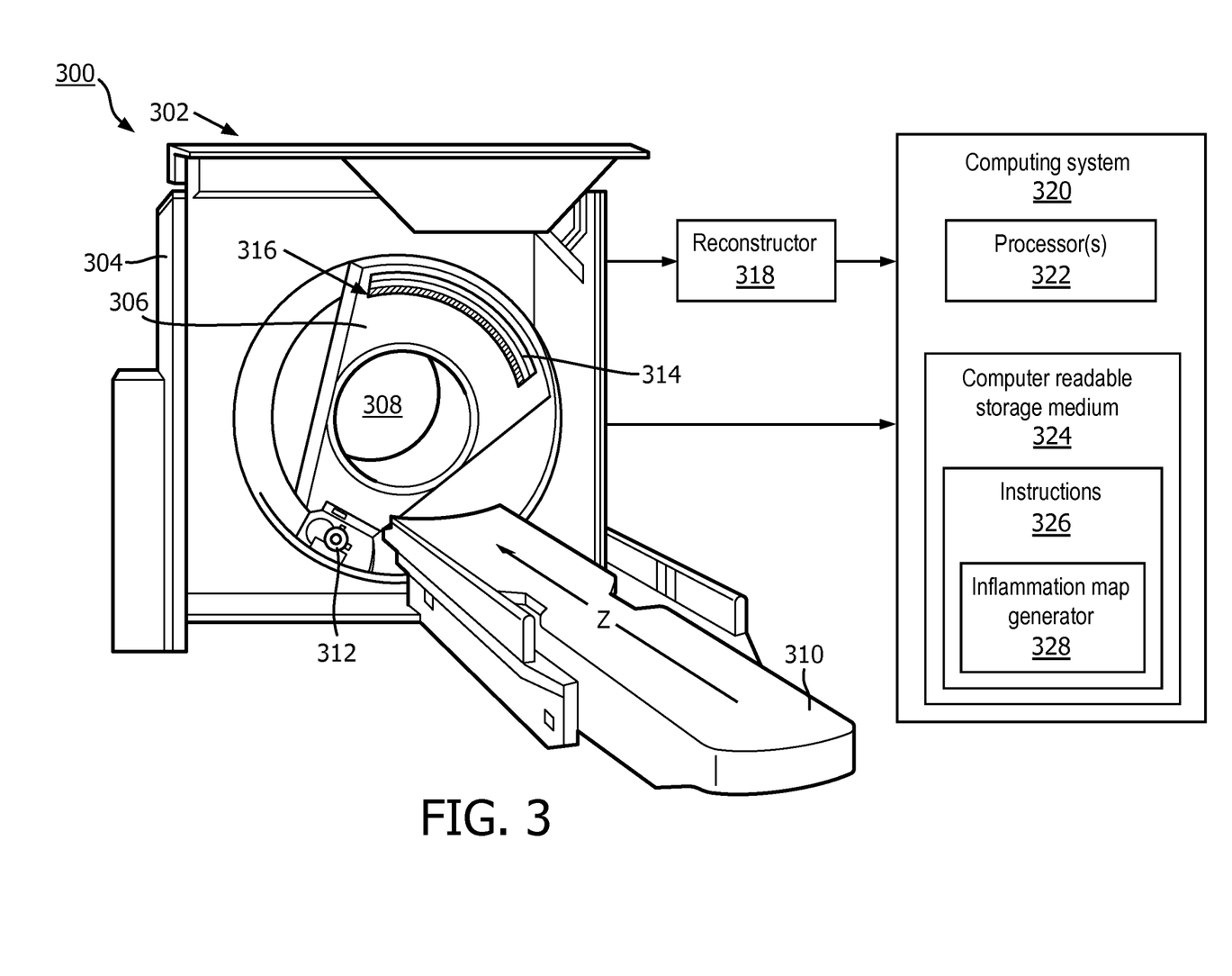
FIG. 3 schematically illustrates a system, including a computing system, with an inflammation map generator, and an imaging system.

FIG. 3 schematically illustrates a system 300 including an imaging system 302 such as a CT scanner configured for spectral (multi-energy) imaging. The imaging system 302 includes a generally stationary gantry 304 and a rotating gantry 306, which is rotatably supported by the stationary gantry 304 and rotates around an examination region 308 about a z-axis. A subject support 310, such as a couch, supports an object or subject in the examination region 308.

A radiation source 312, such as an x-ray tube, is rotatably supported by the rotating gantry 306, rotates with the rotating gantry 306, and emits radiation that traverses the examination region 308. In one instance, the radiation source 312 includes a single broad-spectrum x-ray tube. In another instance, the radiation source 312 includes a single x-ray tube configured to switch between at least two different emission voltages (e.g., 80 kVp and 140 kVp) during scanning. In yet another instance, the radiation source 312 includes two or more x-ray tubes configured to emit radiation having different mean spectra. In still another instance, the radiation source 312 includes a combination thereof.

A radiation sensitive detector array 314 includes a one- or two-dimensional array of rows of detector elements 316 and subtends an angular arc opposite the radiation source 312 across the examination region 308. The radiation sensitive detector array 314 detects radiation traversing the examination region 308 and generates spectral projection data. Where the radiation source 312 includes a single broad-spectrum x-ray tube, the radiation sensitive detector array 314 includes energy-resolving detectors (e.g., direct conversion photon counting detectors, at least two sets of photodiodes with different spectral sensitivities (multi-layer), etc.). With kVp switching and multi-tube configurations, the detector elements 316 can alternatively be non-energy resolving detectors.

A reconstructor 318 receives the spectral projection data and reconstructs spectral volumetric image data such as one or more of a photoelectric image, a Compton scatter image, an iodine image, a virtual non-contrast image, a bone image, a soft tissue image, and/or other basis spectral image. The reconstructor 318 can also generate non-spectral volumetric image data, e.g., by combing the spectral projection data and reconstructing the combined spectral projection data or combining the spectral volumetric image data.

A computing system 320 serves as an operator console. The console 320 includes a human readable output device such as a display and an input device such as a keyboard, mouse, etc. Software resident on the console 320 allows the operator to interact with and/or operate the scanner 302 via a graphical user interface (GUI) or otherwise. The console 320 further includes a processor 322 (e.g., a microprocessor, a controller, a central processing unit (CPU), etc.) and a computer readable storage medium 324, which excludes non-transitory medium, and includes transitory medium such as a physical memory device, etc.

The computer readable storage medium 324 includes instructions 326 for at least an inflammation map generator 328. In a variation, the processor 322 and the computer readable storage medium 324 are part of another computing system, which is separate and remote from (i.e., not part of) the computing system 320. In another variation, the processor 322 may additionally or alternatively execute one or more computer readable instructions carried by a carrier wave, a signal and/or other transitory medium.

The inflammation map generator 328 is configured to process at least the spectral volumetric image data and/or the spectral projection data to generate an inflammation map. As described in greater detail below, the inflammation map generator 328 quantifies the inflammation and/or fat within at least the spectral projection data and/or the spectral volumetric image data by quantifying the contribution of tissue components (e.g., inflammation and/or fat) per pixel at least through the inflammation map. As such, the approach described herein, in one instance, provides a new spectral map (i.e. the inflammation map) that improves the non-invasive assessment of inflammation by CT, e.g., through an improved depiction and quantification of inflammation.

Figure 4:
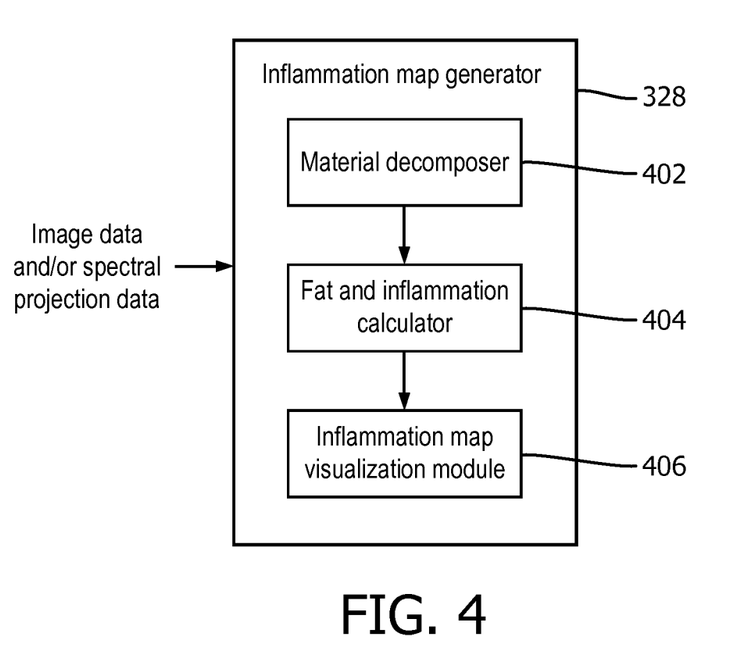
FIG. 4 schematically illustrates an example of the inflammation map generator.

FIG. 4 schematically illustrates an example of the inflammation map generator 328.

The inflammation map generator 328 includes a material decomposer 402. The material decomposer 402 receives spectral data (spectral projection data and/or the spectral volumetric image data) and decomposes the received spectral data at least directly into at least fat and inflammation. The material decomposer 402 outputs a set of vectors representing fat and a set of vectors representing inflammation, with one fat vector and one inflammation vector per voxel.

The inflammation map generator 328 further includes a fat and inflammation concentration calculator 404, which determines the fat and inflammation concentration within a voxel based on the vectors. In one instance, the fat and inflammation concentration calculator 404 determines the concentration of fat and the concentration of inflammation as shown in EQUATION 1:

$$\begin{pmatrix} \text{Low } kv \\ \text{High } kv \end{pmatrix} = \vec{v_0} + \vec{v_{fat}} c_{fat} + \vec{v_{inf}} c_{inf}, \qquad \text{EQUATION 1}$$

where Low kv is the spectral data for the lower energy acquisition, High kv is the spectral data for the higher energy acquisition, $\vec{v_0}$ is a bias vector from an origin (e.g., in the case where there is no bias, $\vec{v_0}$=(0,0)), $\vec{v_{fat}}$ is the vector output by the material decomposer 402 representing fat, $c_{fat}$ is the unknown fat concentration, $\vec{v_{inf}}$ is the vector output by the material decomposer 402 representing inflammation, and $c_{inf}$ is the unknown inflammation concentration. Generally, EQUATION 1 represents a system of linear equations which can be solved simultaneously to determine $c_{fat}$ and $c_{inf}$.

The inflammation map generator 328 further includes a spectral inflammation map visualization module 406. The spectral inflammation map visualization module 406 causes the display to display the quantified fat and inflammation concentrations by visually enhancing (e.g., coloring) each pixel based on its fat and/or inflammation concentration, $c_{fat}$ and $c_{inf}$. For example, in one instance, a pixel containing only fat is colored a first or darker shade of gray, a pixel containing only inflammation is colored a second or lighter shade of gray, and a pixel containing both fat and inflammation is colored a shade of gray therebetween, where the shade of gray is closer to the first shade if the pixel contains more inflammation than fat and is closer to the second shade if the pixel contains more fat than inflammation.

Figure 5:
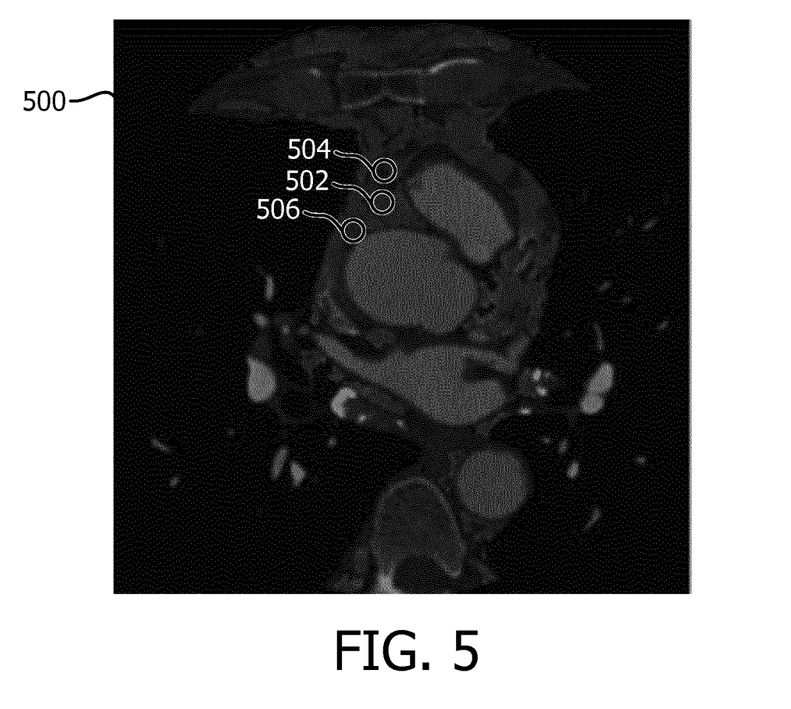
FIG. 5 illustrates an example CT image of a heart with one region of interest including mostly fat and another region of interest including mostly inflammation.

This is shown in FIG. 5, which depicts a CT image 500 with a first ROI 502, a second ROI 504, and a third ROI 506. The first ROI 502 has a higher inflammation concentration and as a result appears lighter than the second ROI 504 which has higher fat concentration. The third ROI 506 comprises both fat and inflammation and as a result appears as a shade of gray between the gray values corresponding to the first ROI 502 and the second ROI 504. In this example, the first ROI 502 and the second ROI 504 are located at substantially the same position as the first ROI 102 and the second ROI 104 depicted in FIG. 1. As shown in FIG. 1, the voxels within the first ROI 102 and the second ROI 104 are substantially the same shade of gray. As a result, it is difficult to distinguish fat from inflammation in the image of FIG. 1, whereas the voxels within the first ROI 502 and the second ROI 504 clearly comprise different shades of gray, which distinguishes fat from inflammation.

Figure 6:
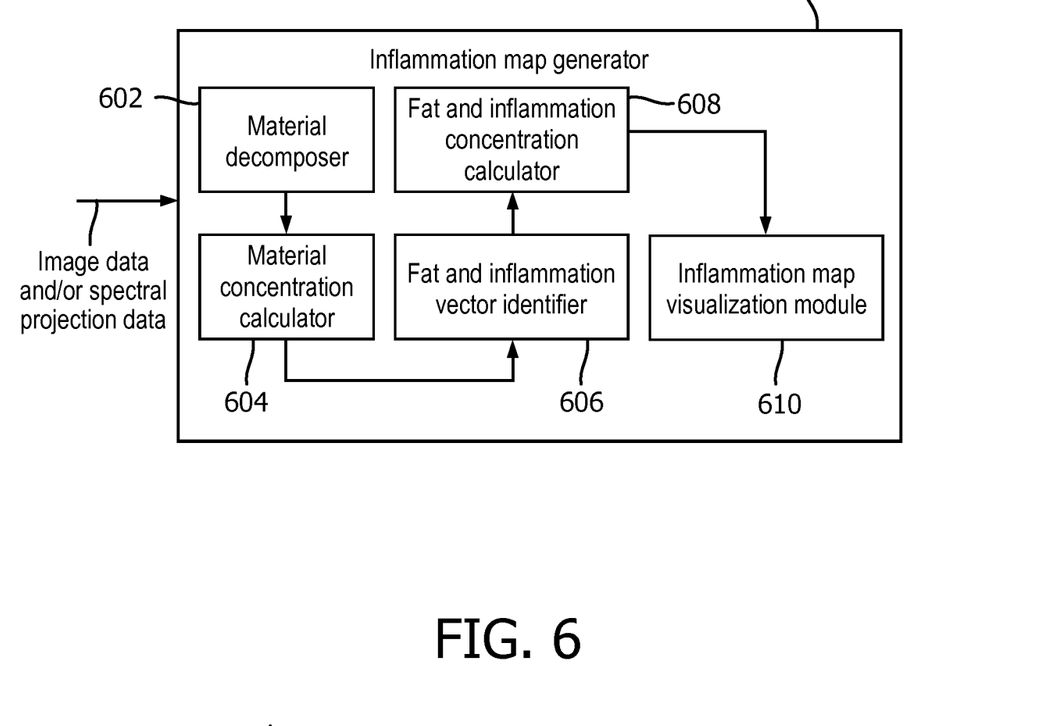
FIG. 6 schematically illustrates another example of the inflammation map generator.

FIG. 6 schematically illustrates another example of the inflammation map generator 328.

In this example, the material decomposer 602 decomposes the input spectral data into two-basis materials (e.g., iodine and water) or components (e.g., the photo-electric effect and Compton scattering). The material decomposer 602 outputs a set of vectors representing one basis and a set of vectors representing another basis, with one vector of each for each voxel.

The inflammation map generator 328 further includes a material concentration calculator 604. The material concentration calculator 604, for a given two-basis decomposition (e.g., photo-electric effect and Compton scattering as shown below), finds the concentrations of each basis for each voxel, e.g., as shown in EQUATION 2:

$$\begin{pmatrix} PhotoE \\ CScatter \end{pmatrix} = \vec{v_0} + \overrightarrow{v_{PhotoE}} c_{PhotoE} + \overrightarrow{v_{CScatter}} c_{CScatter},$$ EQUATION 2 where PhotoE is the photoelectric effect spectral data, CScatter is the Compton scattering spectral data, $\overrightarrow{v_{PhotoE}}$ is the vector generated by the material concentration calculator 604 representing the photoelectric effect, $c_{PhotoE}$ is the unknown concentration for the photoelectric effect, $\overrightarrow{v_{CScatter}}$ is the vector generated by the material concentration calculator 605 representing the Compton scattering, and $c_{CScatter}$ is the unknown concentration for the Compton scattering.

The inflammation map generator 328 further includes a fat and inflammation vector identifier 606. The fat and inflammation vector identifier 606 identifies fat and inflammation vectors with a two-basis diagram. The fat and inflammation vectors can be learned from training data or from the subject using prior knowledge (e.g., the location of inflammation and healthy fat).

Figure 7:
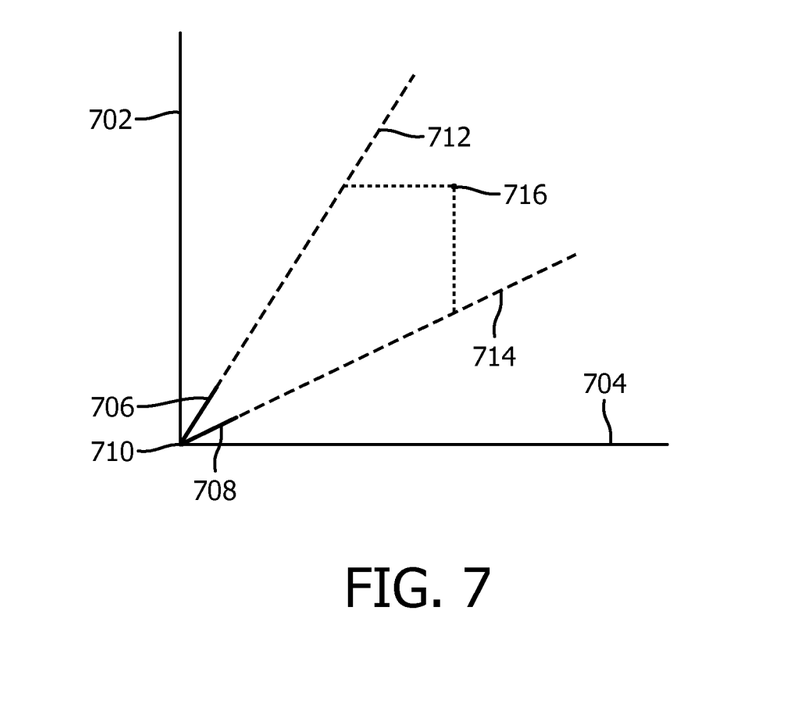
FIG. 7 illustrates a vectorial separation plot.

The inflammation map generator 328 also includes a fat and inflammation concentration calculator 608. The fat and inflammation concentration calculator 608 determines the concentrations of fat and inflammation within a given voxel conceptually using a vectorial separation technique as shown in FIG. 7. Generally, the vectorial separation technique determines the concentration of fat and inflammation within a voxel based on aligning a graphical location of fat and/or inflammation for a given voxel with the corresponding fat and/or inflammation vector. In FIG. 7 a first axis 702 represents a first basis and a second axis 704 represents a second basis represents a second basis (e.g., Photo-Electric and Compton Scattering).

FIG. 7 further shows a first vector 706 which corresponds to inflammation and a second vector 708 which corresponds to fat. The two vectors meet at point 710 which represents the bias of the two vectors from the origin. In this case the basis from the origin is zero (0). FIG. 7 also shows first extrapolation 712 of the first vector 706 and a second extrapolation 714 of the second vector 708. Based on the extrapolations 712 and 714, a concentration of fat and/or inflammation can be determined for a given voxel 716 having known values corresponding to the first and second basis 702 and 704.

In one instance, the fat and inflammation concentration calculator 608 determines the concentration of fat and the concentration of inflammation using a vectorial separation technique as shown in EQUATION 3:

$$\vec{v} = \vec{v_0} + \vec{v_{fat}} c_{fat} + \vec{v_{inf}} c_{inf},$$ EQUATION 3 where $\vec{v}$ is the representation of the voxel in the 2D coordinate system defined by the material decomposition and given the pixel value, 2D coordinates with $\overrightarrow{v_{PhotoE}}$ and $\overrightarrow{v_{CScatter}}$ as the axis, is equal to $$\begin{pmatrix} \overrightarrow{v_{PhotoE}} c_{PhotoE} \\ \overrightarrow{v_{CScatter}} c_{CScatter} \end{pmatrix}$$

in the coordinate system defined by $\vec{v_{fat}}$ and $\vec{v_{inf}}$, $\vec{v_0}$ represents bias from the origin, $\vec{v_{fat}}$ is the vector representing fat identified by the fat and inflammation vector identifier 606, $c_{fat}$ is the unknown concentration of fat, $\vec{v_{inf}}$ is the vector representing inflammation identified by the fat and inflammation vector identifier 606, and $c_{inf}$ is the unknown concentration of inflammation.

The inflammation map generator 328 further includes a spectral inflammation map visualization module 610. The spectral inflammation map visualization module 610 causes the display to display the quantified fat and inflammation concentrations by coloring each pixel within the spectral projection data and/or the spectral volumetric image data based on its fat and/or inflammation concentration.

Figure 8:
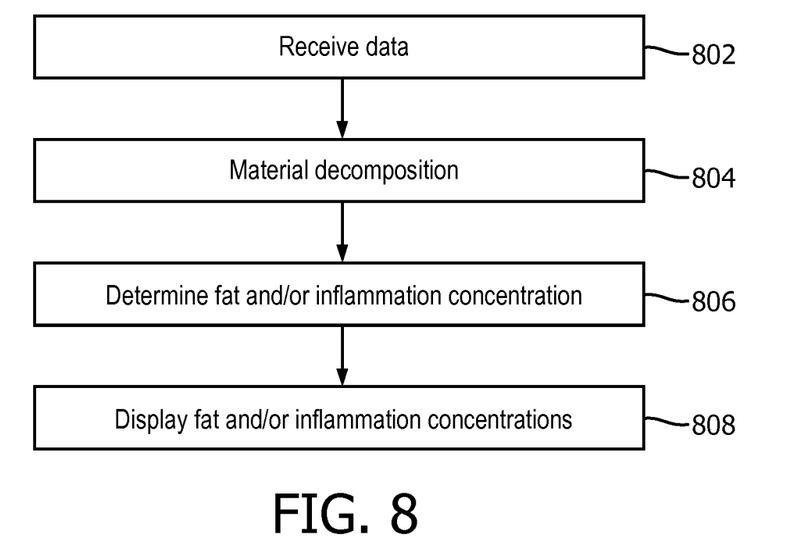
FIG. 8 illustrates an example method in accordance with an embodiment herein.

FIG. 8 illustrates an example method in accordance with an embodiment described herein.

At 802, spectral data (i.e. spectral projection data or spectral volumetric image data) is received, as described herein and/or otherwise.

At 804, the spectral data is materially decomposed, generating a set of vectors for two different bases, as described herein and/or otherwise.

At 806, the vectors representing each basis are used to obtain the concentration of fat and/or inflammation within a voxel, as described herein and/or otherwise.

At 808, the determined fat and inflammation within a voxel is displayed as described herein and/or otherwise.

Figure 9:
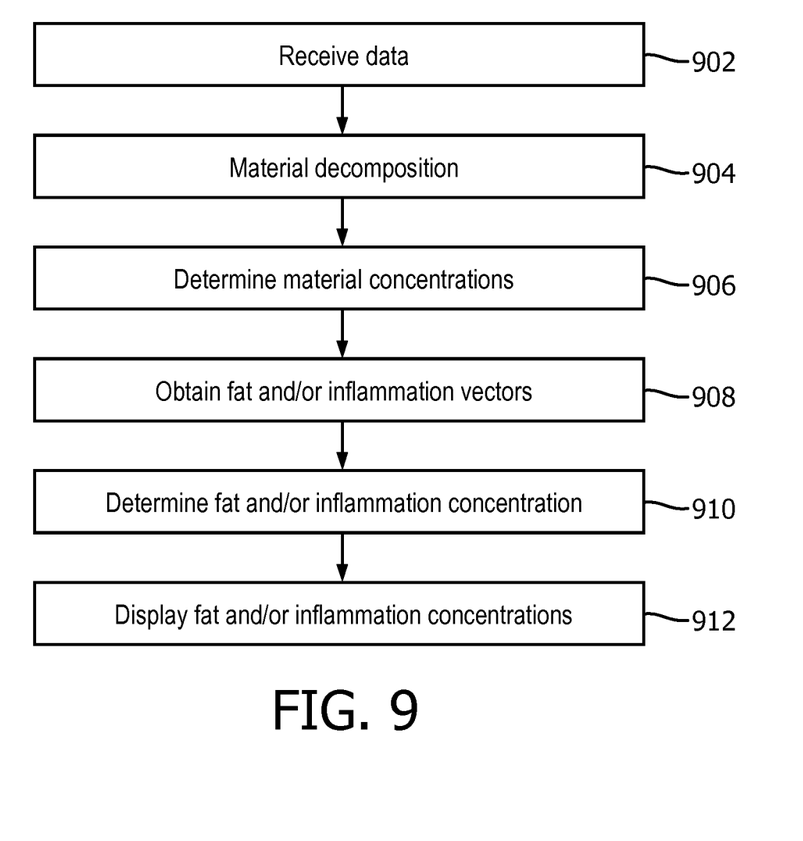
FIG. 9 illustrates an example method in accordance with another embodiment herein.

FIG. 9 illustrates an example method in accordance with an embodiment described herein.

At 902, spectral data (i.e. spectral projection data or spectral volumetric image data) is received, as described herein and/or otherwise.

At 904, the spectral data is materially decomposed, generating a set of vectors for two different bases, as described herein and/or otherwise.

At 906, the vectors representing each basis are used to obtain the concentration of each basis within a voxel, as described herein and/or otherwise.

At 908, locations within the two basis diagrams having known fat or inflammation are used to obtain vectors representing fat and inflammation as described herein and/or otherwise.

At 910, the concentration of fat and/or inflammation within a voxel is determined as described herein and/or otherwise.

At 912, the determined fat and inflammation within a voxel is displayed as described herein and/or otherwise.

It is to be appreciated that the ordering of the above acts is not limiting. As such, other orderings are contemplated herein. In addition, one or more acts may be omitted and/or one or more additional acts may be included.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system, comprising:
   a memory configured to store a plurality of instructions;
   a processor configured to execute the plurality of instructions to:
   receive at least one of spectral projection data and spectral volumetric image data;
   decompose the at least one of spectral projection data and spectral volumetric image data using a two-basis decomposition to generate a set of vectors for each basis of two bases in the two-basis decomposition, the set of vectors being represented in the at least one of spectral projection data and spectral volumetric image data; and
   determine, from the set of vectors for each basis of the two bases in the two-basis decomposition, a concentration of at least inflammation within a voxel, by:
     computing, from the set of vectors for each basis of the two bases in the two-basis decomposition, a concentration, within the voxel, of each basis of the two bases in the two-basis decomposition; and
     determining, from the concentration of each basis of the two bases in the two-basis decomposition, the concentration of the at least inflammation within the voxel; and
   a display configured to display the determined concentration of the at least inflammation.

2. The system of claim 1, further comprising:
   an imaging system, including:
   a radiation source configured to emit X-ray radiation;
   a detector array configured to detect X-ray radiation and generate the spectral projection data; and
   a reconstructor configured to reconstruct a signal and generate the spectral volumetric image data.

3. The system of claim 1, wherein one material of the two-basis decomposition is fat and the other is inflammation.

4. The system of claim 3, wherein the processor is further configured to:
   determine the concentration of at least inflammation within the voxel by solving:

$$\begin{pmatrix} \text{Low } kv \\ \text{High } kv \end{pmatrix} = \vec{v_0} + \vec{v_{fat}} c_{fat} + \vec{v_{inf}} c_{inf},$$

where Low kv is spectral volumetric image data from a low energy image, High kv is spectral volumetric image data from a high energy image, $\vec{v_0}$ is a bias from an origin, $\vec{v_{fat}}$ is a vector representing fat, $c_{fat}$ is a fat concentration, $\vec{v_{inf}}$ is a vector representing inflammation, and $c_{inf}$ is an inflammation concentration.

5. The system of claim 1, wherein one basis of the two-basis decomposition is photo-electric effect and the other is Compton scattering.

6. The system of claim 5, wherein the processor is further configured to:
   determine a concentration of at least one of photo-electric effect and Compton scattering by solving:

$$\begin{pmatrix} PhotoE \\ CScatter \end{pmatrix} = \vec{v_0} + \vec{v_{PhotoE}} c_{PhotoE} + \vec{v_{CScatter}} c_{CScatter},$$

where PhotoE is a photoelectric effect, CScatter is a Compton scattering, $\vec{v_{PhotoE}}$ is a vector representing the photoelectric effect, $C_{PhotoE}$ is a concentration of the photoelectric effect, $\vec{v_{CScatter}}$ is a vector representing the Compton scattering, and $c_{CScatter}$ is a concentration of the Compton scattering,
   wherein the processor is further configured to:
   determine the concentration of the at least inflammation within the voxel by solving $$\vec{v} = \vec{v_0} + \vec{v_{fat}} c_{fat} + \vec{v_{inf}} c_{inf},$$

where $\vec{v}$ is a representation of the voxel in a 2D coordinate system defined by the two-basis decomposition and given a pixel value, wherein 2D coordinates with $\vec{v_{PhotoE}}$ and $\vec{v_{CScatter}}$ as an axis, is equal to $$\begin{pmatrix} \vec{v_{PhotoE}} c_{PhotoE} \\ \vec{v_{CScatter}} c_{CScatter} \end{pmatrix}$$

in a coordinate system defined by $\vec{v_{fat}}$ and $\vec{v_{inf}}$, $\vec{v_0}$ represents a bias from an origin, $\vec{v_{fat}}$ is a vector representing fat, $c_{fat}$ is a concentration of fat, $\vec{v_{inf}}$ is a vector representing inflammation, and $c_{inf}$ is a concentration of inflammation.

7. The system of claim 1, wherein the concentration of at least inflammation is displayed by coloring a pixel based on the concentration of the at least inflammation within a corresponding voxel, where a voxel representing inflammation is displayed in a first color, a voxel representing fat is displayed in a second different color, and a voxel representing a combination of inflammation and fat is displayed in a third different color from a range of colors between the first and second colors.

8. The system of claim 1, wherein determining of the concentration of the at least inflammation includes determining a concentration of fat and the concentration of inflammation.

9. A method, comprising:
receiving at least one of spectral projection data and spectral volumetric image data;
decomposing the at least one of spectral projection data and spectral volumetric image data using a two-basis decomposition to generate a set of vectors for each basis of two bases in the two-basis decomposition, the set of vectors being represented in the at least one of spectral projection data and spectral volumetric image data; and
determining, from the set of vectors for each basis of the two bases in the two-basis decomposition, a concentration of at least inflammation within a voxel, by:
computing, from the set of vectors for each basis of the two bases in the two-basis decomposition, a concentration, within the voxel, of each basis of the two bases in the two-basis decomposition; and
determining, from the concentration of each basis of the two bases in the two-basis decomposition, the concentration of the at least inflammation within the voxel; and
displaying the determined concentration of the at least inflammation.

10. The method of claim 9, wherein one material of the two-basis decomposition is fat and the other is inflammation.

11. The method of claim 10, further comprising:
determining the concentration of at least inflammation within the voxel by solving:

$$\begin{pmatrix} \text{Low } kv \\ \text{High } kv \end{pmatrix} = \vec{v_0} + \vec{v_{fat}} c_{fat} + \vec{v_{inf}} c_{inf},$$

where Low kv is spectral volumetric image data from a low energy image, High kv is spectral volumetric image data from a high energy image, $\vec{v_0}$ is a bias from an origin, $\vec{v_{fat}}$ is a vector representing fat, $c_{fat}$ is a fat concentration, $\vec{v_{inf}}$ is a vector representing inflammation, and $c_{inf}$ is an inflammation concentration.

12. The method of claim 9, wherein one basis of the two-basis decomposition is photo-electric effect and the other is Compton scattering.

13. The method of claim 12, further comprising:
determining a concentration of at least one of photoelectric effect and Compton scattering by solving:

$$\begin{pmatrix} \text{PhotoE} \\ \text{CScatter} \end{pmatrix} = \vec{v_0} + \vec{v_{PhotoE}} c_{PhotoE} + \vec{v_{CScatter}} c_{CScatter},$$

where PhotoE is a photoelectric effect, CScatter is a Compton scattering, $\vec{v_{PhotoE}}$ is a vector representing the photoelectric effect, $c_{PhotoE}$ is a concentration of the photoelectric effect, $\vec{v_{CScatter}}$ is a vector representing the Compton scattering, and $c_{CScatter}$ is a concentration of the Compton scattering.

14. The method of claim 13, further comprising:
determining the concentration of the at least inflammation within the voxel by solving $$\vec{v} = \vec{v_0} + \vec{v_{fat}} c_{fat} + \vec{v_{inf}} c_{inf},$$

where $\vec{v}$ is the representation of the voxel in a 2D coordinate system defined by the material decomposition and given a pixel value, wherein 2D coordinates with $\vec{v_{PhotoE}}$ and $\vec{v_{CScatter}}$ as an axis, is equal to $$\begin{pmatrix} \vec{v_{PhotoE}} c_{PhotoE} \\ \vec{v_{CScatter}} c_{CScatter} \end{pmatrix}$$

in a coordinate system defined by $\vec{v_{fat}}$ and $\vec{v_{inf}}$, $\vec{v_0}$ represents a bias from an origin, $\vec{v_{fat}}$ is a vector representing fat, $c_{fat}$ is a concentration of fat, $\vec{v_{inf}}$ is a vector representing inflammation, and $c_{inf}$ is a concentration of inflammation.

15. The method of claim 9, wherein the concentration of at least inflammation is displayed by coloring a pixel based on the concentration of the at least inflammation within a corresponding voxel, where a voxel representing inflammation is displayed in a first color, a voxel representing fat is displayed in a second different color, and a voxel representing a combination of inflammation and fat is displayed in a third different color from a range of colors between the first and second colors.

16. A non-transitory computer readable storage medium encoded with computer readable instructions, which, when executed by a processor of a computing system, causes the processor to:
receive at least one of spectral projection data and spectral volumetric image data;
decompose the at least one of spectral projection data and spectral volumetric image data using a two-basis decomposition to generate a set of vectors for each basis of two bases in the two-basis decomposition, the set of vectors being represented in the at least one of spectral projection data and spectral volumetric image data; and
determine, from the set of vectors for each basis of the two bases in the two-basis decomposition, a concentration of at least inflammation within a voxel, by:
computing, from the set of vectors for each basis of the two bases in the two-basis decomposition, a concentration, within the voxel, of each basis of the two bases in the two-basis decomposition; and
determining, from the concentration of each basis of the two bases in the two-basis decomposition, the concentration of the at least inflammation within the voxel; and
display the determined concentration of the at least inflammation.

17. The non-transitory computer readable storage medium of claim 16, wherein one material of the two-basis decomposition is fat and the other is inflammation.

18. The non-transitory computer readable storage medium of claim 16, wherein one basis of the two-basis decomposition is photo-electric effect and the other is Compton scattering.

19. The non-transitory computer readable storage medium of claim 16, wherein executing the computer readable instructions further causes the processor to learn at least inflammation vector identity form at least one of training data and a location of at least known inflammation within a subject.

20. The non-transitory computer readable storage medium of claim 16, wherein the concentration of at least inflammation is displayed by coloring a pixel based on the concentration of the at least inflammation within a corresponding voxel, where a voxel representing inflammation is displayed in a first color, a voxel representing fat is displayed in a second different color, and a voxel representing a combination of inflammation and fat is displayed in a third different color from a range of colors between the first and second colors.

* * * * *